United States Patent
Relan et al.

(10) Patent No.: US 12,167,917 B2
(45) Date of Patent: Dec. 17, 2024

(54) SYSTEM AND METHOD FOR DETECTION AND MAPPING OF NEAR FIELD CONDUCTION IN SCAR TISSUE

(71) Applicant: St. Jude Medical, Cardiology Division, Inc., St. Paul, MN (US)

(72) Inventors: Jatin Relan, Bordeaux (FR); Steven Kim, New York, NY (US); Mark Hagfors, North Oaks, MN (US); Don Curtis Deno, Andover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 466 days.

(21) Appl. No.: 17/604,220

(22) PCT Filed: May 7, 2020

(86) PCT No.: PCT/US2020/031775
§ 371 (c)(1),
(2) Date: Oct. 15, 2021

(87) PCT Pub. No.: WO2020/227469
PCT Pub. Date: Nov. 12, 2020

(65) Prior Publication Data
US 2022/0202346 A1      Jun. 30, 2022

Related U.S. Application Data

(60) Provisional application No. 62/845,433, filed on May 9, 2019.

(51) Int. Cl.
A61B 5/367 (2021.01)
A61B 5/287 (2021.01)
A61B 5/339 (2021.01)

(52) U.S. Cl.
CPC .............. *A61B 5/367* (2021.01); *A61B 5/287* (2021.01); *A61B 5/339* (2021.01)

(58) Field of Classification Search
CPC .......... A61B 5/367; A61B 5/339; A61B 5/347
See application file for complete search history.

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| EP | 3 923 796 A1 | 12/2021 |
| WO | 2017/151347 A1 | 9/2017 |
| WO | WO 2017/151347 | * 9/2017 |

OTHER PUBLICATIONS

International Preliminary Report on Patentability received for PCT Application Serial No. PCT/US20/31775 mailed on Nov. 18, 2021, 9 pages.

*Primary Examiner* — George R Evanisko
(74) *Attorney, Agent, or Firm* — Wiley Rein LLP

(57) ABSTRACT

Pulmonary vein isolation has become a first-line treatment for symptomatic drug refractory atrial fibrillation (AF). In the context of PVI procedures, linear ablation lesions are delivered in order to achieve PV isolation. Electrophysiological maps from data collected by high density (HD) grid catheters can be used to identify conduction gaps associated within circumferential pulmonary vein isolation lesions.

15 Claims, 11 Drawing Sheets

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2017/0049348 A1* | 2/2017 | Deno ................. A61B 18/1492 |
| 2017/0096198 A1 | 4/2017 | Peter |
| 2018/0296111 A1 | 10/2018 | Deno et al. |
| 2020/0077908 A1 | 3/2020 | Hagfors et al. |

* cited by examiner

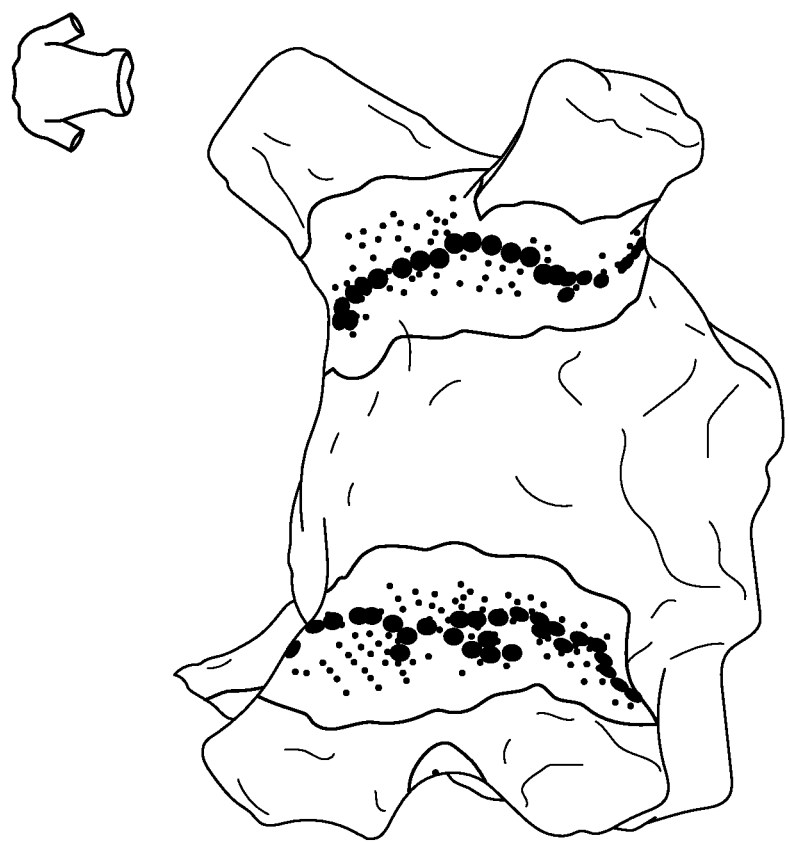
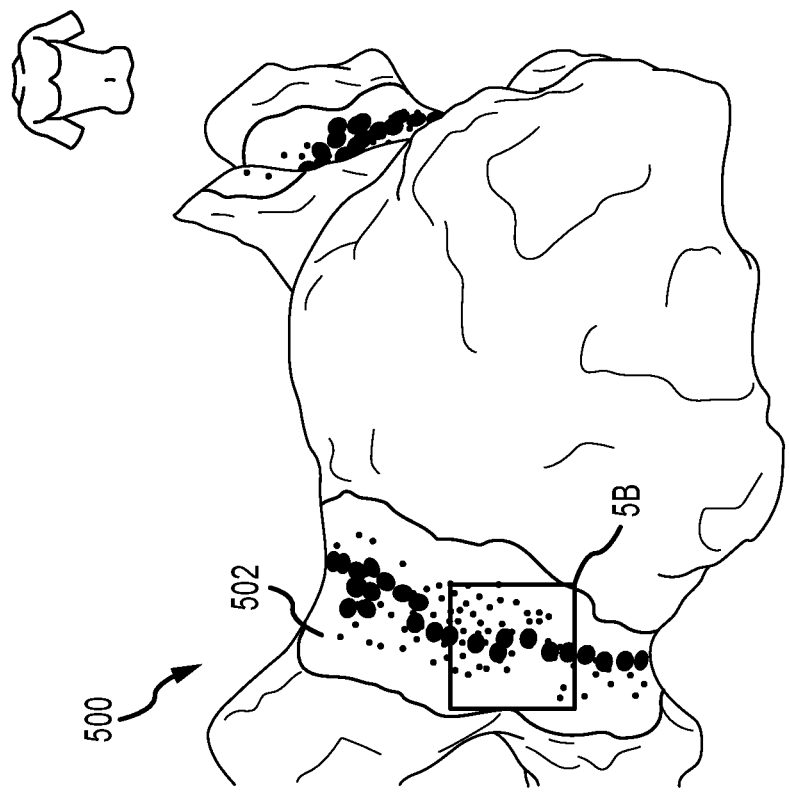
FIG.5A

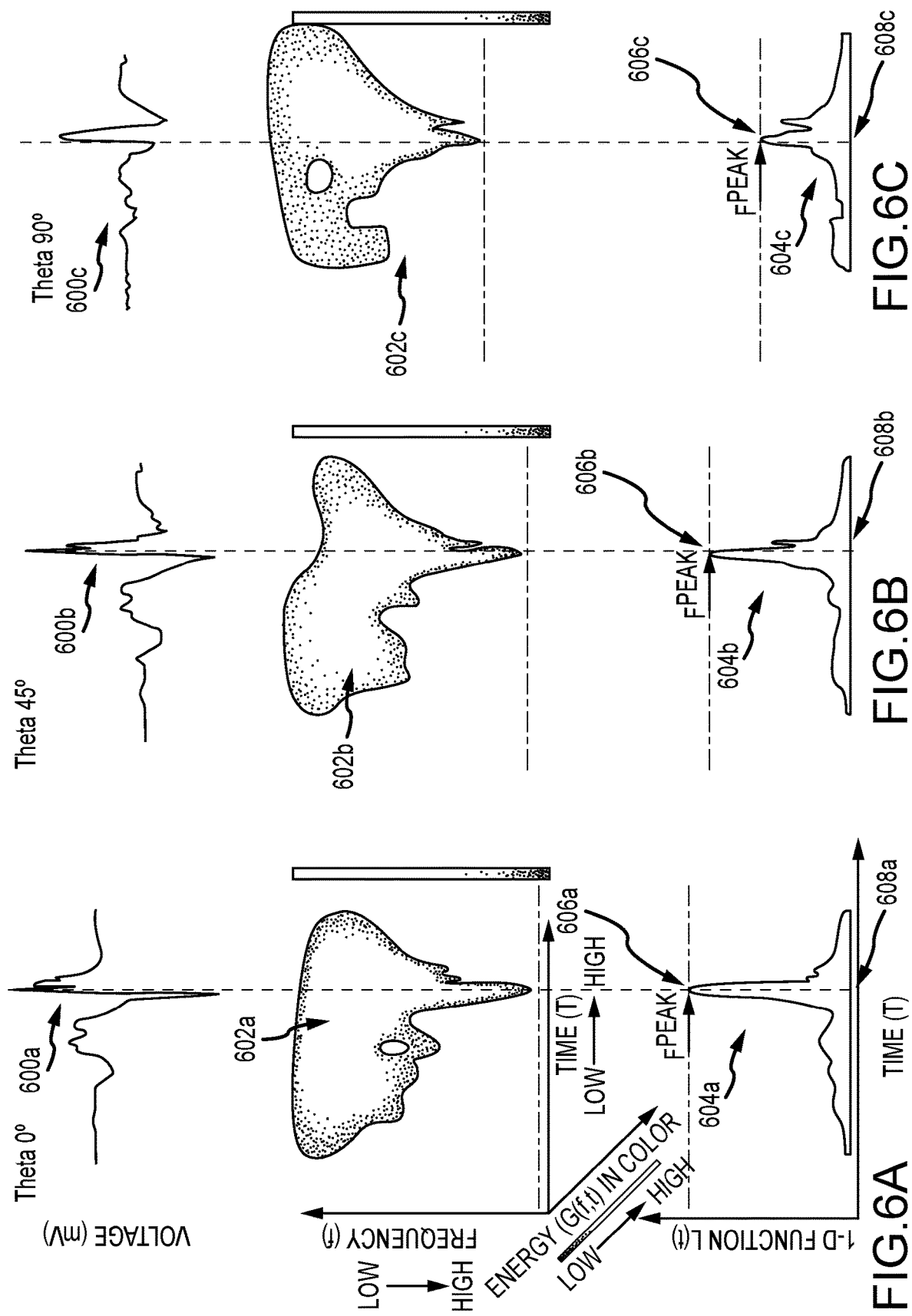

SYSTEM AND METHOD FOR DETECTION AND MAPPING OF NEAR FIELD CONDUCTION IN SCAR TISSUE

CROSS-REFERENCE TO RELATED APPLICATIONS

This application claims the benefit of U.S. provisional application No. 62/845,433, filed 9 May 2019, which is hereby incorporated by reference as though fully set forth herein.

BACKGROUND

The present disclosure relates generally to cardiac mapping, such as may be performed in cardiac diagnostic and therapeutic procedures. In particular, the present disclosure relates to systems, apparatuses, and methods for mapping and visualizing local conductive activity in either native scar or ablative lesion-induced scar, such as circumferential pulmonary vein isolation ("PVI") lesions, and conduction activity in low-voltage scar tissue, including the use of data collected by a high density ("HD") grid catheter or other multi-electrode device.

PVI has become a first-line treatment for symptomatic drug refractory atrial fibrillation ("AF"). Patients may, however, require multiple procedures for AF or for organized macro-reentrant tachycardia. Pulmonary vein ("PV") reconnection is one possible cause necessitating follow-on procedures.

More generally, linear ablative lesions may be delivered in order to compartmentalize the cardiac chamber, and eliminate any abnormal conductive activity in the scar. For example, discontinuities in previous ablation lesions may allow for the resumption of arrhythmogenic conduction.

In today's clinical state-of-the-art, voltage mapping is commonly employed to identify regions of live activity in scar. The discrimination of low-voltage conductive activity is often confounded by the presence of far-field content in the source electrogram.

BRIEF SUMMARY

The instant disclosure provides a method of mapping local conductive activity in a lesion. This includes: receiving a plurality of electrophysiology (EP) data points at an electroanatomical mapping system, wherein each EP data point of the plurality of EP data points includes electrophysiological signals measured by a high-density grid catheter; computing, with the electroanatomical mapping system, a metric for each EP data point using the electrophysiological signals for the respective EP data point; and outputting, with the electroanatomical mapping system, a graphical representation that facilitates visualization of one or more conduction gaps in the lesion using the metrics.

In embodiments of the disclosure, the step of receiving a plurality of electrophysiology (EP) data points at an electroanatomical mapping system includes: receiving an EP data set at the electroanatomical mapping system, wherein the EP data set corresponds to an anatomical region; and using the electroanatomical mapping system to bound the EP data set to a region of interest ("ROI") within the anatomical region, wherein the plurality of EP data points fall within the region of interest.

The metric can be a peak-frequency value for the respective EP data point.

In aspects of the disclosure, the method can also include using the electroanatomical mapping system to define an optimized omnipole orientation for each EP data point using the electrophysiological signals for the respective EP data point.

For instance, the electroanatomical mapping system can: compute a plurality of omnipolar electrograms for the respective EP data point using the electrophysiological signals for the respective EP data point; compute a plurality of scalograms corresponding to the plurality of omnipolar electrograms; compute a plurality of peak-frequency functions corresponding to the plurality of scalograms; and define an orientation exhibiting a maximum peak frequency of the plurality of peak-frequency functions as the optimized omnipole orientation for the respective EP data point.

The plurality of scalograms can be computed by applying a continuous wavelet transformation (e.g., a high time-resolution mother wavelet, such as a Paul wavelet) to the plurality of omnipolar electrograms.

To define the orientation exhibiting a maximum peak frequency of the plurality of peak-frequency functions as the optimized omnipole orientation for the respective EP data point, the electroanatomical mapping system can: generate a curve relating peak frequency to omnipole orientation; and define an omnipole orientation at which the curve reaches a maximum as the optimized omnipole orientation for the respective EP data point.

Graphical representations contemplated by the instant disclosure include at least one of a graphical representation a near-field activity map and a graphical representation of a near-field activation map.

The graphical representation of the near-field activity map can depict values of a peak-frequency metric relative to at least one of a near-field frequency threshold and a far-field frequency threshold. Thus, the graphical representation of the near-field activity map can facilitate visualization of the one or more conduction gaps in the lesion by highlighting regions where the peak-frequency metric exceeds the near-field frequency threshold.

The graphical representation of the near-field activation map can depict a plurality of local activation times (LATs), wherein each LAT of the plurality of LATs is computed for an optimized omnipole orientation for a respective EP data point.

The instant disclosure also provides a system for mapping conduction activity in a tissue. The system includes a mapping and visualization module configured to: receive a plurality of electrophysiology (EP) data points, wherein each EP data point of the plurality of EP data points includes electrophysiological signals measured by a high-density grid catheter; compute a metric for each EP data point using the electrophysiological signals for the respective EP data point; and output a graphical representation that facilitates visualization of one or more conduction activities in the tissue using the metrics.

The graphical representation can include at least one of a graphical representation of a near-field activity map and a graphical representation of a near-field activation map.

The metric can include a peak-frequency metric.

The mapping and visualization processor can also be configured to compute the peak-frequency metric for a respective EP data point by: computing a plurality of omnipolar electrograms for the respective EP data point using the electrophysiological signals for the respective EP data point; computing a plurality of scalograms corresponding to the plurality of omnipolar electrograms for the respective EP data point; computing a plurality of peak-frequency functions corresponding to the plurality of scalograms; and identifying an orientation exhibiting a maximum peak frequency of the plurality of peak-frequency functions as an optimized omnipole orientation for the respective EP data point. The peak-frequency metric at the optimized omnipole orientation can then be defined as the peak-frequency metric for the respective EP data point.

It is also contemplated that the mapping and visualization processor can be further configured to: receive an EP data set corresponding to an anatomical region; and bound the EP data set to a region of interest ("ROI") within the anatomical region, wherein the plurality of EP data points fall within the region of interest.

Also disclosed herein is a method of mapping local conduction activity in a tissue, including: receiving a plurality of electrophysiology (EP) data points at an electroanatomical mapping system, wherein each EP data point of the plurality of EP data points includes electrophysiological signals measured by a high-density grid catheter; computing, with the electroanatomical mapping system, a peak-frequency metric at an optimized omnipole orientation for each EP data point using the electrophysiological signals for the respective EP data point; and outputting, via the electroanatomical mapping system, a graphical representation of the peak-frequency metric that facilitates visualization of near-field conduction activity in the tissue.

Still further, the instant disclosure provides a method of mapping conduction gaps in a pulmonary vein isolation lesion set, including: receiving, at an electroanatomical mapping system, an electrogram signal measured by a high-density grid catheter; transforming the electrogram signal into the wavelet domain; computing a one-dimensional peak-frequency function of the transformed electrogram signal; computing a peak-frequency metric of the one-dimensional peak-frequency function; optimizing orientation of a virtual omnipole; and generating one or more of a near-field activity map and an activation map, wherein the near-field activity map and the near-field activation map facilitate visualization of one or more conduction gaps in the pulmonary vein isolation lesion set.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 5A illustrates an electrophysiology map of PVI lesions.

FIGS. 6A, 6B, and 6C are representative electrogram signals, their corresponding scalograms, and their corresponding peak-frequency functions.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for generating electrophysiology maps. For purposes of illustration, aspects of the disclosure will be described with reference to cardiac electrophysiology procedures. More specifically, aspects of the disclosure will be described in the context of the creation of maps that aid a practitioner in identifying conduction gaps in a lesion set, such as a circumferential PVI lesion. Further, these illustrative maps will be discussed in conjunction with intracardiac electrograms collected using a high density (HD) grid catheter, such as the Advisor™ HD grid mapping catheter from Abbott Laboratories (Abbott Park, Illinois) and an electroanatomical mapping system, such as the EnSite Precision™ cardiac mapping system, also from Abbott Laboratories.

Those of ordinary skill in the art will understand, however, how to apply the teachings herein in other contexts and/or with respect to other devices and systems. For instance, the teachings herein may also be used to good advantage to map local conduction activity in low-voltage scar tissue.

Figure 1:
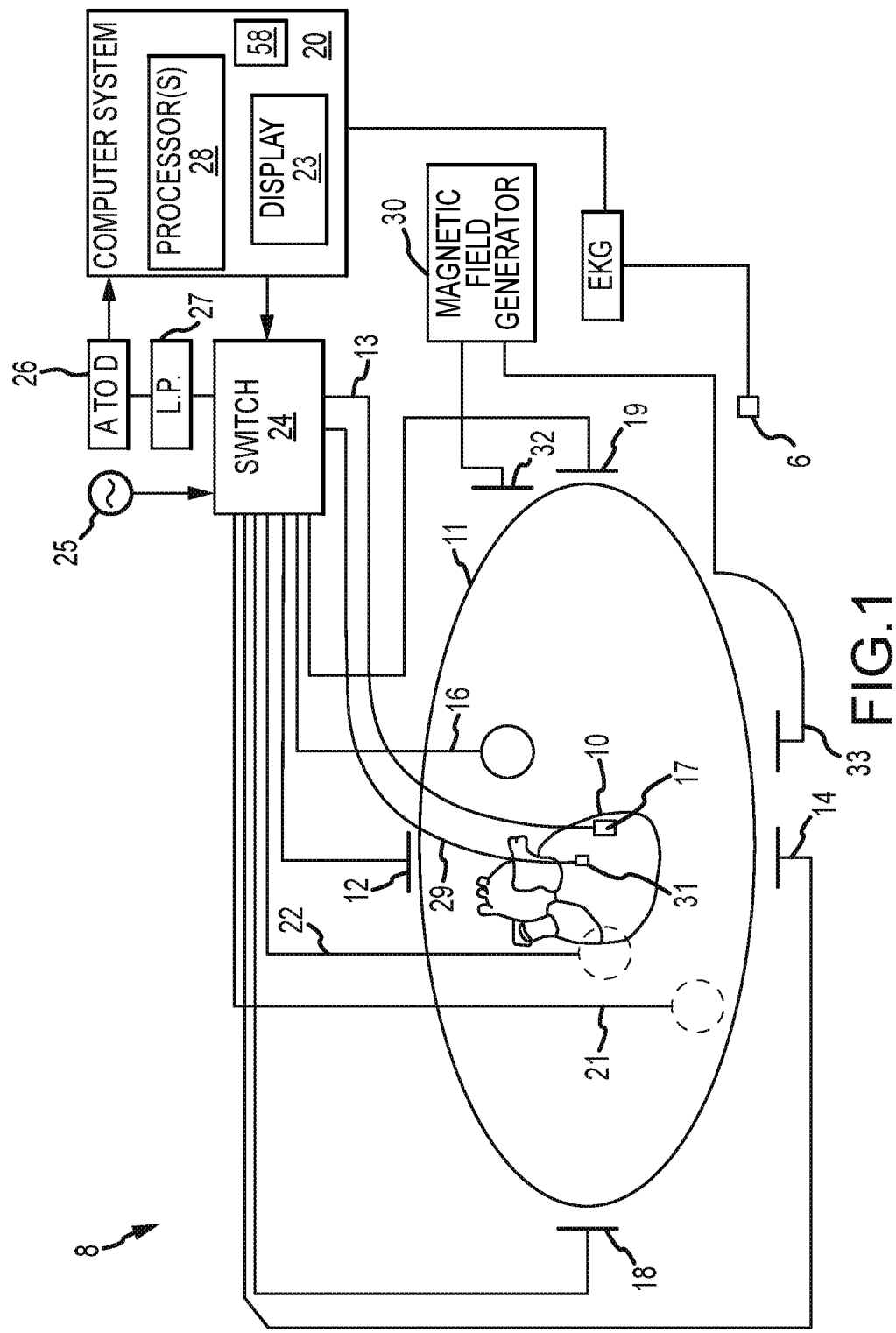
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, system 8 determines the location, and in some aspects the orientation, of objects, typically within a three-dimensional space, and expresses those locations as position information determined relative to at least one reference. This is referred to herein as "localization."

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
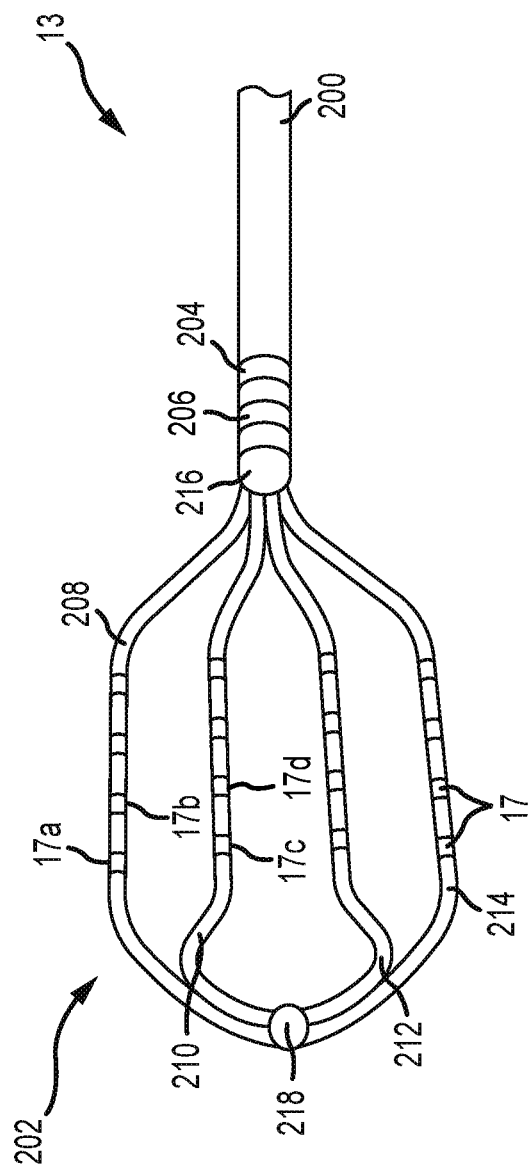
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214. For purposes of easy reference in this description, FIG. 3A provides alphanumeric labels for electrodes 17.

As those of ordinary skill in the art will recognize, any two neighboring electrodes 17 define a bipole. Thus, the 16 electrodes 17 on catheter 13 define a total of 42 bipoles—12 along splines (e.g., between electrodes 17a and 17b, or between electrodes 17c and 17d), 12 across splines (e.g., between electrodes 17a and 17c, or between electrodes 17b and 17d), and 18 diagonally between splines (e.g., between electrodes 17a and 17d, or between electrodes 17b and 17c).

Figure 3B:
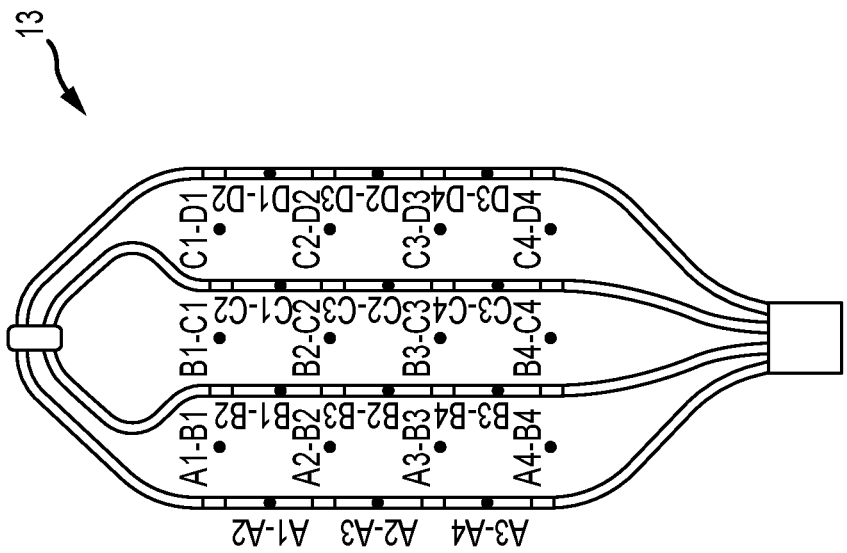
FIGS. 3A and 3B provide alphanumeric labeling conventions for electrodes carried by a multi-electrode catheter and the bipoles associated therewith.
Figure 3A:
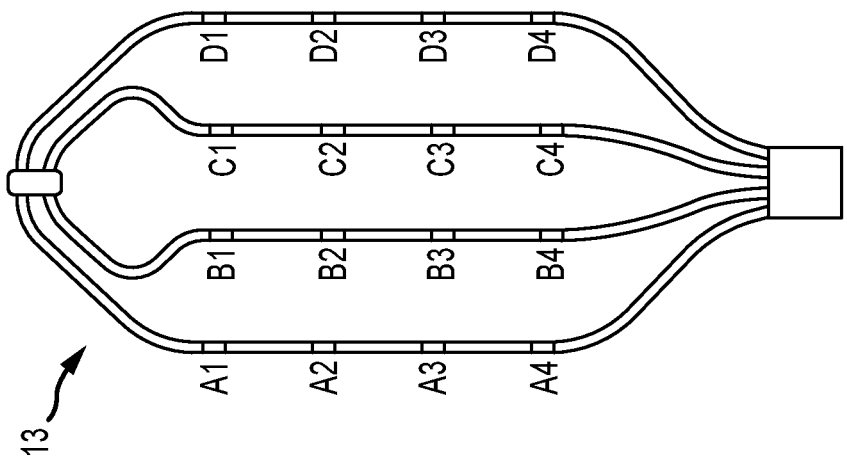

For ease of reference in this description, FIG. 3B provides alphanumeric labels for the along- and across-spline bipoles. FIG. 3B omits alphanumeric labels for the diagonal bipoles, but this is only for the sake of clarity in the illustration. It is expressly contemplated that the teachings herein can also be applied with respect to the diagonal bipoles.

Any bipole can, in turn, be used to generate a bipolar electrogram according to techniques that will be familiar to those of ordinary skill in the art. Moreover, these bipolar electrograms can be combined (e.g., linearly combined) to generate electrograms, again including activation timing information, in any direction of the plane of catheter 13 by computing an E-field loop for a clique of electrodes. United States patent application publication no. 2018/0296111 (the '111 publication), which is hereby incorporated by reference as though fully set forth herein, discloses details of computing an E-field loop for a clique of electrodes on a HD grid catheter. These are referred to herein as "omnipoles" or "virtual bipoles."

In any event, catheter 13 can be used to simultaneously collect a plurality of electrophysiology data points for the various bipoles defined by electrodes 17 thereon, with each such electrophysiology data point including both localization information (e.g., position and orientation of a selected bipole) and an electrogram signal for the selected bipole. For purposes of illustration, methods according to the instant disclosure will be described with reference to individual electrophysiology data points collected by catheter 13. It should be understood, however, that the teachings herein can be applied, in serial and/or in parallel, to multiple electrophysiology data points collected by catheter 13.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In aspects of the disclosure, system 8 can be a hybrid system that incorporates both impedance-based (e.g., as described above) and magnetic-based localization capabilities. Thus, for example, system 8 can also include a magnetic source 30, which is coupled to one or more magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings. Likewise, those of ordinary skill in the art will appreciate that, for purposes of localizing catheter 13 within the magnetic fields so generated, can include one or more magnetic localization sensors (e.g., coils).

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation (Marlborough, Massachusetts), the CARTO® navigation and location system of Biosense Webster, Inc. (Irvine, California), the AURORA® system of Northern Digital Inc. (Waterloo, Ontario), Sterotaxis, Inc.'s NIOBE® Magnetic Navigation System (St. Louis, Missouri), as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure generally relate to generating electrophysiology maps, and in particular to maps of near-field conduction activity. Such maps may be useful to identify conduction gaps in ablation lesions (e.g., PVI lesions), as well as to identify conduction activity in low-voltage scar tissue. Graphical representations of such electrophysiology maps can also be output, for example on display 23.

System 8 can therefore include a mapping and visualization module 58. Advantageously, visualization of such electrophysiology maps can aid a practitioner in recognizing where a cardiac activation wavefront is "leaking" through confined channels present in a lesion set (e.g., from the pulmonary veins into the atrium or vice versa). Because the teachings herein thus facilitate mapping and visualizing Lesion Induced Channeled Activities, the term "LICA" can be used to refer to the metrics disclosed herein when the instant teachings are applied to the context of identifying conduction gaps within the lesion.

Figure 4:
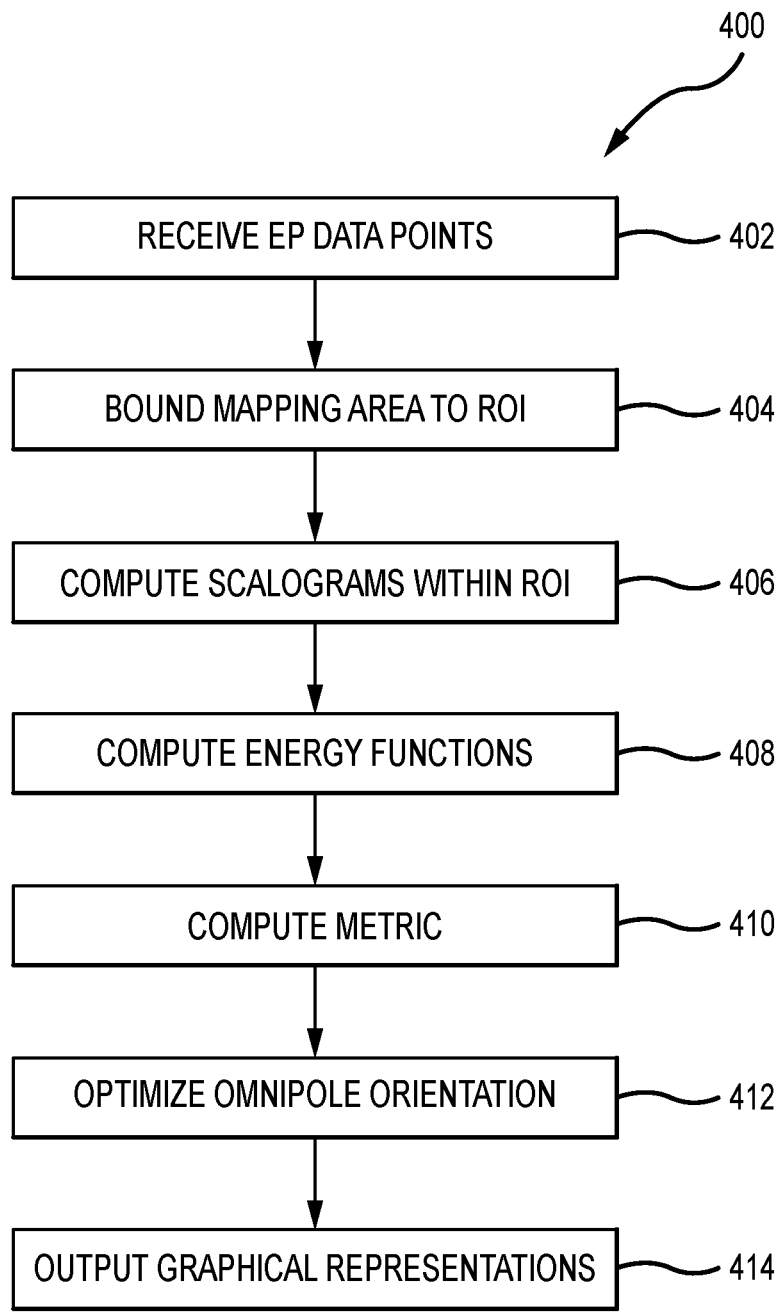
FIG. 4 is a flowchart of representative steps that can be carried out according to aspects of the instant disclosure in connection with mapping conduction gaps in a circumferential PVI lesion set.

One exemplary method, which illustrates aspects of the instant disclosure in the context of mapping conduction gaps within a circumferential PVI lesion set, will be explained with reference to the flowchart of representative steps presented as FIG. 4. In some embodiments, for example, flowchart 400 may represent several exemplary steps that can be carried out by electroanatomical mapping system 8 of FIG. 1 (e.g., by processor 28 and/or mapping and visualization module 58). It should be understood that the representative steps described below can be either hardware- or software-implemented. For the sake of explanation, the term "signal processor" is used herein to describe both hardware- and software-based implementations of the teachings herein.

In block 402, system 8 receives a plurality of electrophysiology (EP) data points, each of which includes both localization information and electrophysiology information (e.g., one or more electrogram signals S(t) measured using electrodes 17 on catheter 13). According to aspects of the instant disclosure, the electrogram signals S(t) are omnipolar electrograms; as discussed above and in the '111 publication, omnipolar electrogram signals can be computed for a clique of electrodes 17 in any direction of the plane of catheter 13 using constituent bipolar electrograms.

Block 404 bounds the mapping area to a Region of Interest ("ROI"), which results in a "region of interest map" or "focused map" containing a subset of the plurality of EP data points received in block 402. In embodiments of the disclosure, the ROI can be defined by the user, such as within a preset distance of a previously-created lesion.

Figure 5B:
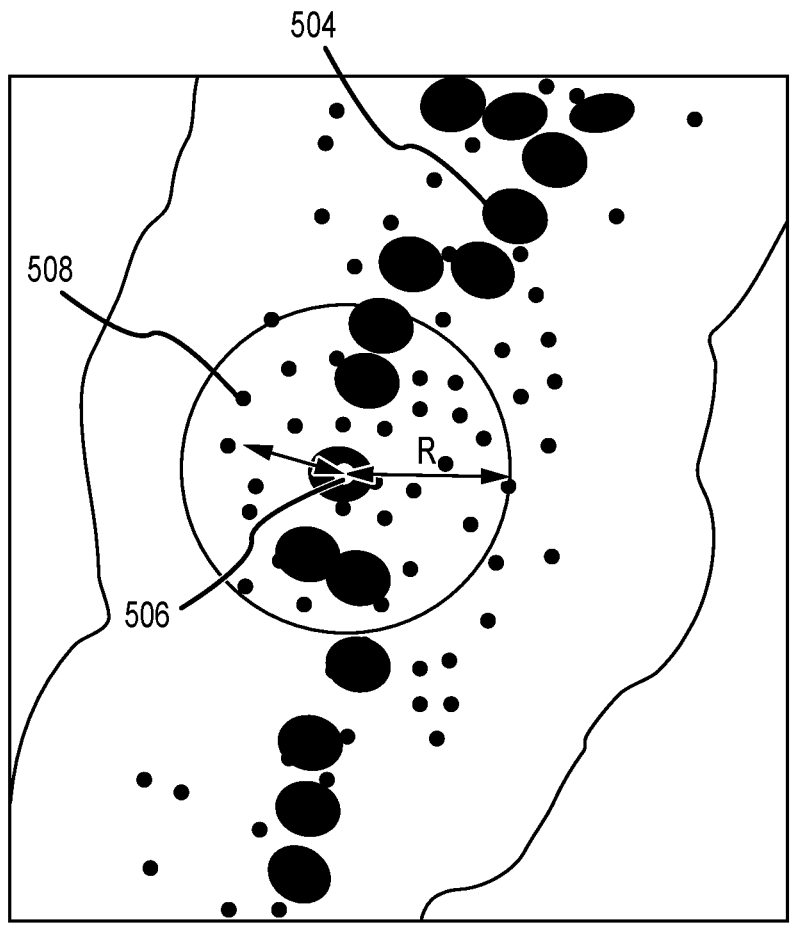
FIG. 5B is a close-up of the Region of Interest (ROI) bounded by box 5B in FIG. 5A.

FIGS. 5A and 5B illustrate the bounding process in the context of circumferential PVI lesions. FIG. 5A is a graphical representation of an electrophysiology map 500, including circumferential PVI ablation lines 502, while FIG. 5B is a close-up view of the region bounded by box 5B in FIG. 5A. As shown in FIG. 5B, electrophysiology map 500 includes a plurality of lesion tags 504 corresponding to PVI ablation lines 502.

A center-point 506 is defined for each lesion tag 504. A radius R is also defined; in embodiments of the disclosure, R can be user defined. System 8 then identifies any EP data points (e.g., 508) falling within radius R of center-point 506 based, for example, on the geodesic or Euclidean distance of each EP data point from center-point 506. If the distance between a given EP data point 508 and center-point 506 is less than R, then EP data point 508 is added to the focused map. In general, therefore, the focused map will contain EP data points falling within radius R of a center-point 506.

An analogous approach can be applied when the teachings herein are applied in the context of mapping conduction in regions of low-voltage scar tissue.

Other approaches to defining the ROI are also contemplated. For instance, a practitioner can manually define the ROI, such as by interacting with a graphical user interface on display 23.

In further embodiments of the disclosure, the ROI can be defined using a template anatomical model. That is, a template anatomical model, with predefined ROIs, can be registered and warped (via rigid and/or non-rigid transformation algorithms) to a patient-specific model generate by system 8.

It may also be desirable to define ROIs around regions of slow conduction and/or regions with random dispersion of activation direction.

In block 406, the electrogram signals S(t) for the EP data points within the focused map are transformed into the wavelet domain, thereby computing a plurality of scalograms of the electrogram signals S(t). A scalogram is a three-dimensional plot that shows the energy G of a signal as a function of frequency f and time t (e.g., G(f, t)).

In embodiments of the disclosure, system 8 applies a continuous wavelet transformation ("CWT") to the electrogram signals using a high time-resolution mother wavelet, such as a Paul wavelet. A CWT provides a redundant, but finely detailed, description of a signal (e.g., electrogram signal S(t)) in terms of both time and frequency. CWTs are particularly helpful in tackling problems involving signal identification and detection of hidden transients (hard to detect, short-lived elements of a signal).

By way of illustration, FIGS. 6A through 6C depict omnipolar electrogram signals 600a, 600b, 600c and their corresponding scalograms 602a, 602b, 602c for three different omnipoles computed using signals measured by catheter 13. More specifically, FIG. 6A is an omnipole oriented at 0 degrees (e.g., nominally perpendicular to shaft 200 and splines 208, 210, 212, 214), FIG. 6B is an omnipole oriented at 45 degrees (e.g., nominally diagonal relative to shaft 200 and splines 208, 210, 212, 214), and FIG. 6C is an omnipole oriented at 90 degrees (e.g., nominally parallel to shaft 200 and splines 208, 210, 212, 214).

In block 408, system 8 computes one-dimensional (1D) functions (e.g., 604a, 604b, 604c) of the scalograms computed in block 406. According to aspects of the disclosure, the 1D function is a one-dimensional peak-frequency function (frequency (on the y-axis) vs time (on the x-axis))

$$L(t)=\max(f), \text{ if } G(f,t) > \text{Energy}^{Threshold}$$

where f ranges from about 0 Hz to about 1000 Hz and Energy$^{Threshold}$ is a preset (and optionally user-defined) noise threshold, such as a normalized value of about 0.2.

In block 410, system 8 computes one or more metrics (e.g., LICA metrics, in the case of mapping lesion gaps) using the 1D functions computed in block 408. For instance, in embodiments of the disclosure, a peak-frequency metric $F^{Peak}$ can be defined as the frequency at which the peak-frequency function L(t) has its maximum (e.g., the frequencies of peaks 606a, 606b, 606c in FIGS. 6A through 6C, respectively).

It should be understood that metrics can be computed for individual omnipole orientations. For instance, the peak-frequency metric $F^{Peak}$ for the 0 degree omnipole of FIG. 6A, the peak-frequency metric $F^{Peak}$ for the 45 degree omnipole of FIG. 6B, and the peak-frequency metric $F^{Peak}$ for the 90 degree omnipole of FIG. 6C are all different.

It is also contemplated, however, to compute a metric for an optimized omnipole orientation in block 412. In particular, using the peak-frequency functions for several omnipole orientations as input, system 8 can generate a curve that relates the metric (e.g., peak-frequency metric $F^{Peak}$) to omnipole orientation. Two representative such curves 700a, 700b are shown in FIG. 7.

In embodiments of the disclosure, curves 700a, 700b can be generated by computing the peak-frequency metric $F^{Peak}$ for omnipole orientations in one degree steps. It is also contemplated, however, to generate curves 700a, 700b in multiple resolutions. In a coarse resolution, peak-frequency metrics $F^{Peak}$ can be computed for omnipole orientations in larger steps (e.g., about twenty degrees) to find a range within which curves 700a, 700b likely reach their maxima. Then, in a fine resolution, peak frequency metrics $F^{Peak}$ can be computed within that range in more granular steps (e.g., about one degree). This multi-resolution approach advantageously reduces computing overhead necessary to identify the optimized omnipole orientation.

Figure 7:
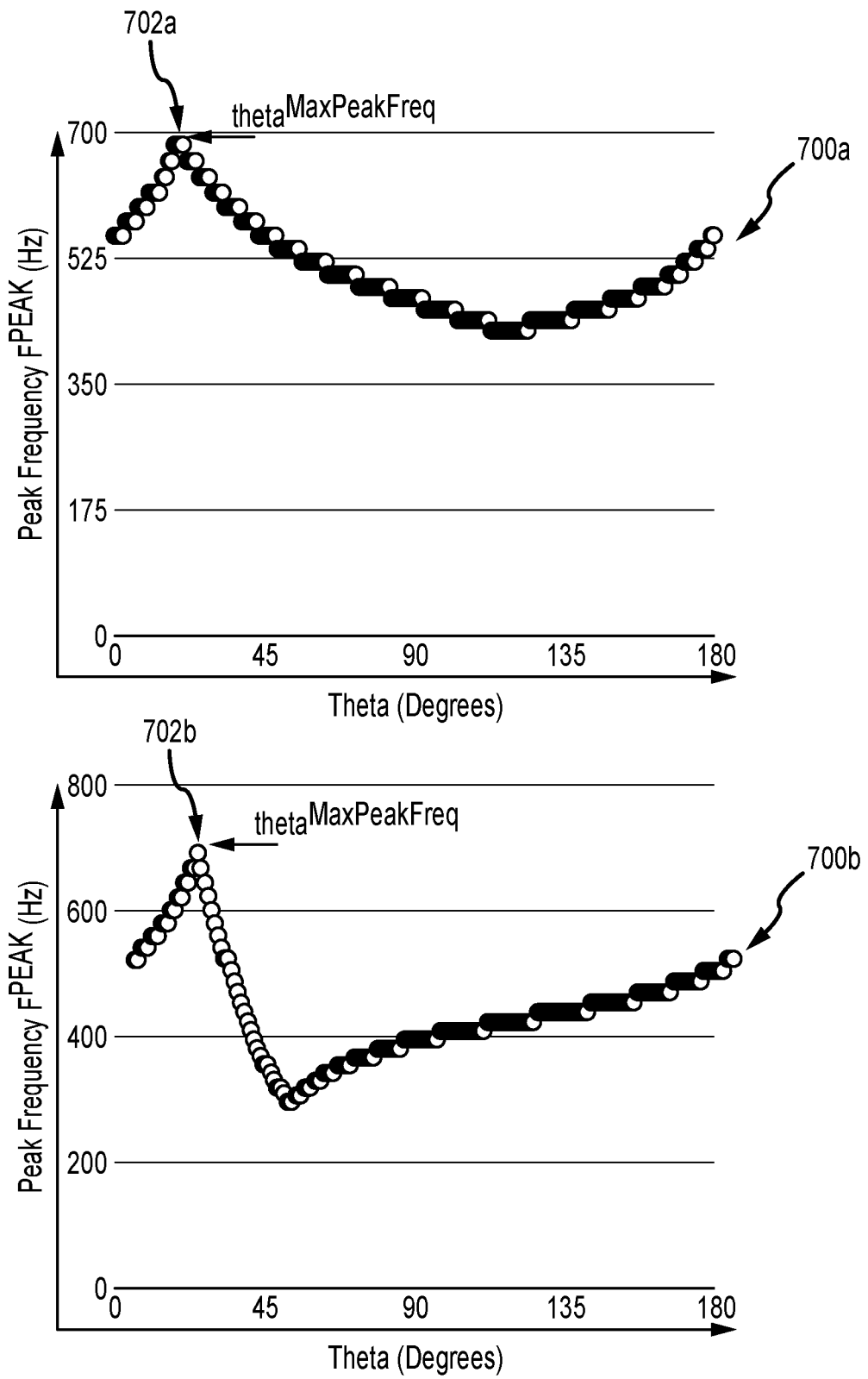
FIG. 7 depicts curves that relate peak-frequency function maxima to omnipole orientation.

In general, however, once the curve is generated, system 8 defines the orientation at which the curve is maximized (e.g., that is, the orientation corresponding to the maximum peak-frequency metric $F^{Peak}$), shown as 702a, 702b in FIG. 7, as the optimized omnipole orientation.

System 8 can output one or more graphical representations of the metric (e.g., at the optimized omnipole orientation and/or at other omnipole orientations) in block 414. The graphical representations disclosed herein include, without limitation, near-field activity maps and near-field activation maps.

A near-field activity map depicts how the peak-frequency metric $F^{Peak}$ relates to near- and far-field frequency thresholds. For instance, a given EP data point within the ROI can be colored red if its peak-frequency metric $F^{Peak}$ exceeds a near-field frequency threshold, colored grey if its peak-frequency metric $F^{Peak}$ is less than a far-field frequency threshold, and colored according to a colorscale if its peak-frequency metric $F^{Peak}$ is between the near- and far-field frequency thresholds. In embodiments of the disclosure, the near-field frequency threshold can be about 800 Hz and the far-field frequency threshold can be about 500 Hz, though it should be understood that these values can also be user-adjustable.

Figure 8:
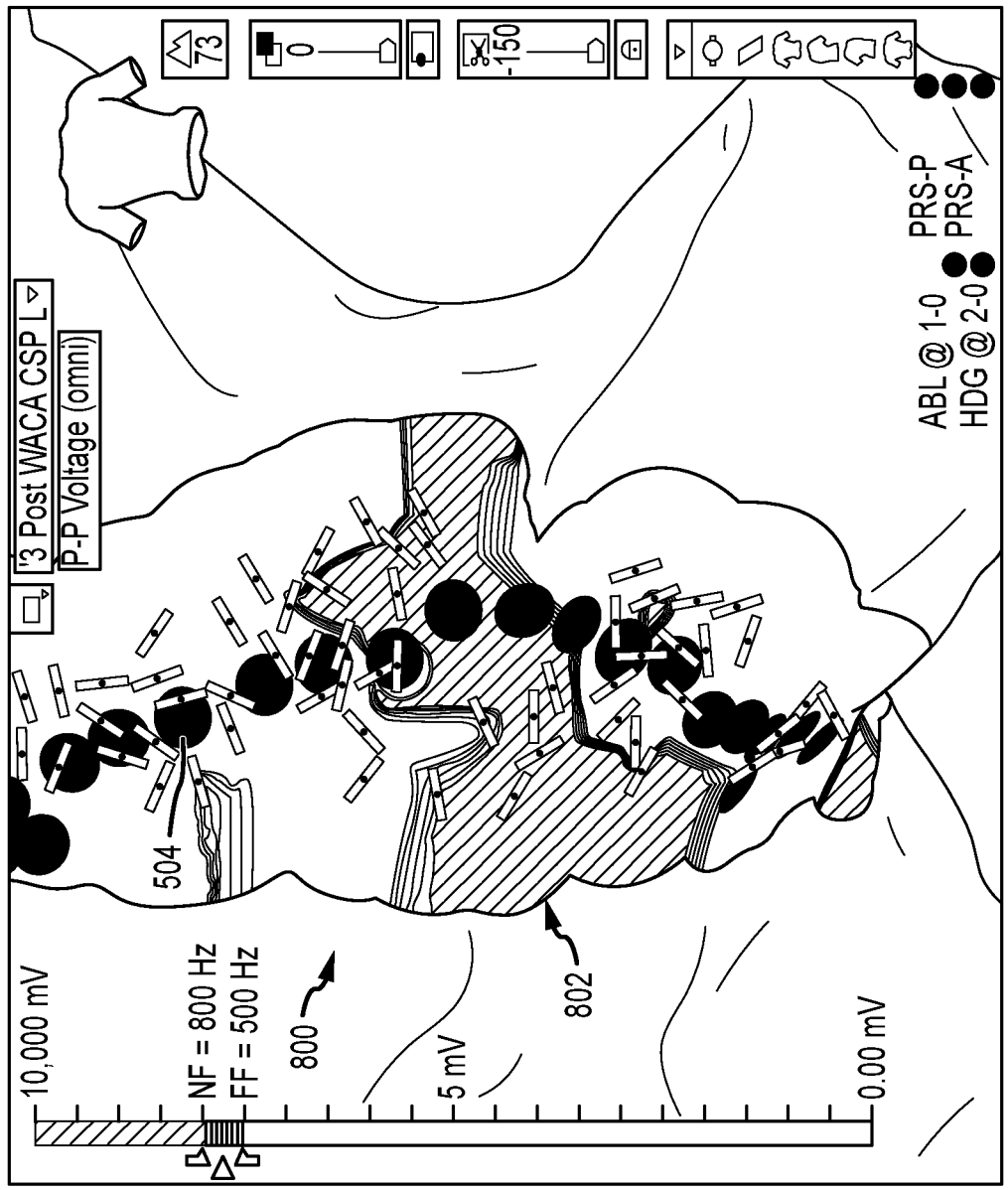
FIG. 8 is a representative near-field activity map for a circumferential PVI lesion set according to aspects of the instant disclosure.

FIG. 8 is a representative near-field activity map 800. Region 802, where the peak-frequency metric $F^{Peak}$ exceeds the near-field frequency threshold on both sides of lesion tags 504, is a potential gap in the circumferential PVI lesion set, allowing an activation wavefront to leak between the PV and the atrium.

Near-field activation maps display the local activation times ("LATs") for EP data points within the ROI and can be computed using optimally-oriented omnipoles. In embodiments of the disclosure, the LAT is the time at which the peak-frequency function L(t) for the optimized orientation omnipole exhibits its peak (e.g., analogous to times 608a, 608b, and 608c in FIGS. 6A-6C, respectively).

Figure 9:
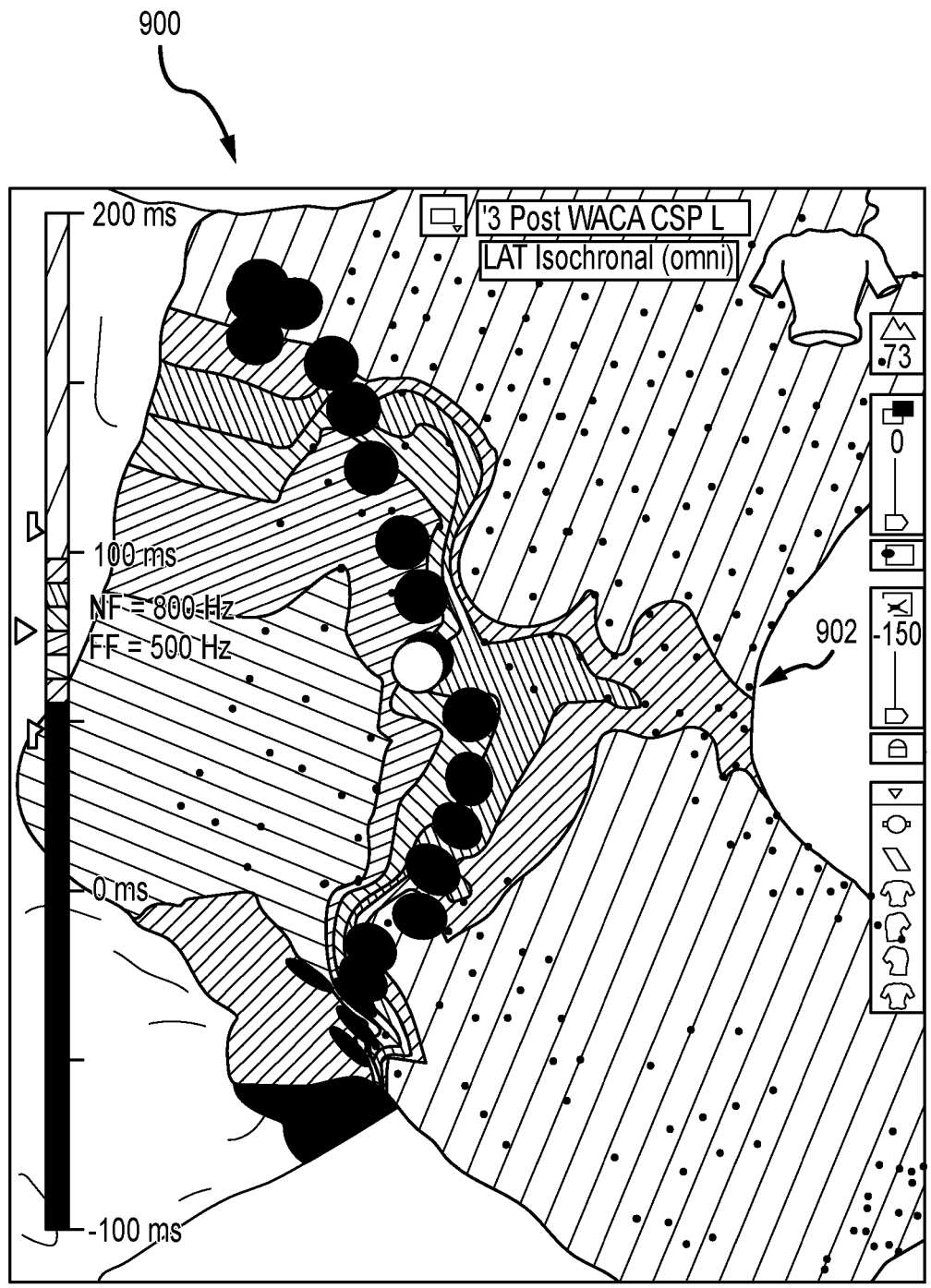
FIG. 9 is a representative near-field activation map for a PVI lesion according to aspects of the instant disclosure.

FIG. 9 is a representative near-field activation map 900. Region 902 shows activation leaking from the atrium towards the pulmonary vein, and thus evidences a conduction gap in the circumferential PVI lesion.

Figure 10:
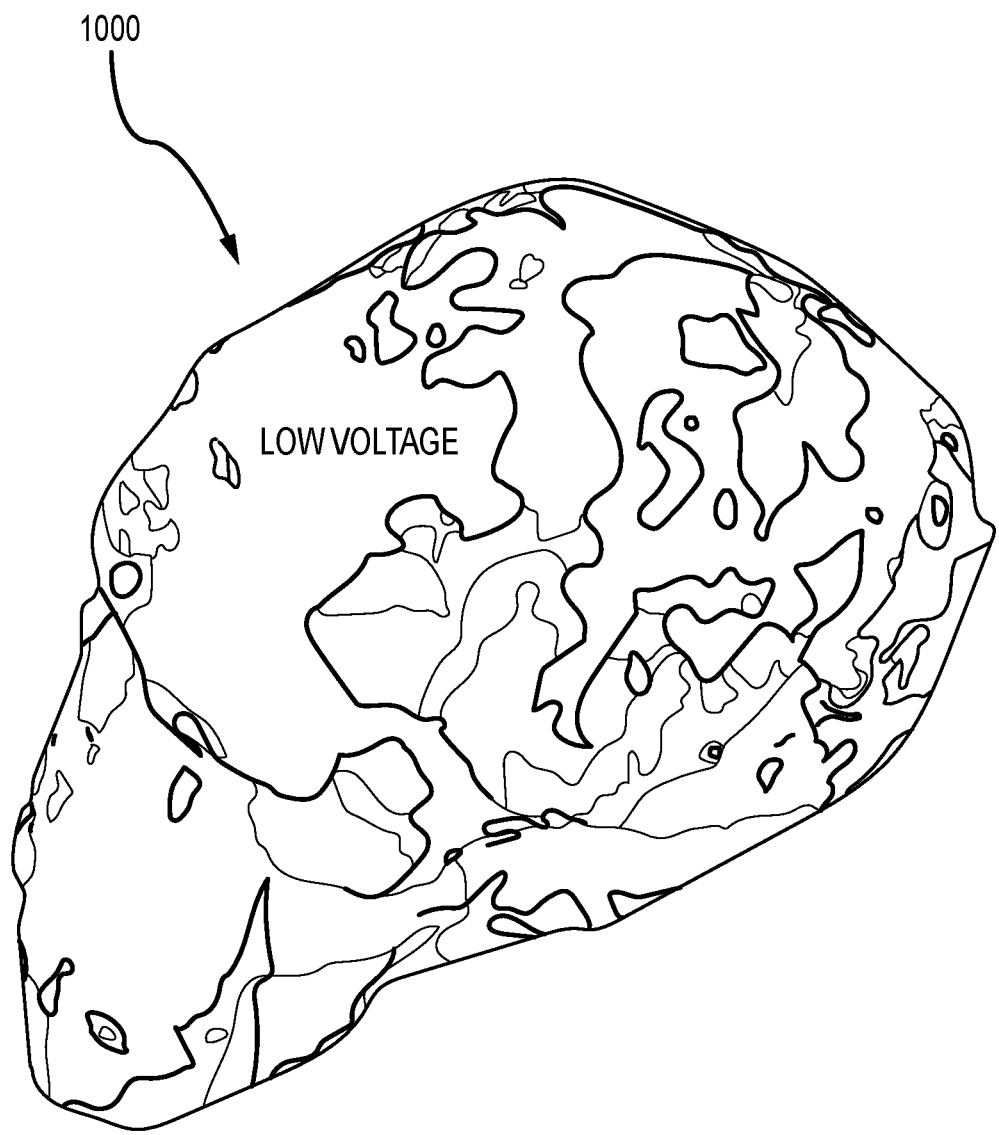
FIG. 10 is a representative near-field activity map for a low voltage region according to aspects of the instant disclosure.

To illustrate application of the teachings herein to mapping conduction activity in low-voltage scar tissue, FIG. 10 is a representative near-field activity map 1000 for a low voltage ROI.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, the teachings herein need not be limited to an ROI. Indeed, they could equally well be applied to a global electrophysiology map.

As yet another example, the graphical representations can be output not only at the optimized omnipole orientation, but also for other omnipole orientations. For example, United States patent application publication no. 2020/0077908, which is hereby incorporated by reference as though fully set forth herein, discloses various graphical user interface conventions that may be applied to selecting omnipole orientations for display.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping local conductive activity in a lesion comprising:
   receiving a plurality of electrophysiology (EP) data points at an electroanatomical mapping system including a high-density grid catheter and a display, wherein each EP data point of the plurality of EP data points includes electrophysiological signals measured by the high-density grid catheter;
   computing, with the electroanatomical mapping system, a metric for each EP data point using the electrophysiological signals for the respective EP data point;
   using the electroanatomical mapping system to define an optimized omnipole orientation for the respective EP data point using the electrophysiological signals for the respective EP data point by:
      computing a plurality of omnipolar electrograms for the respective EP data point using the electrophysiological signals for the respective EP data point;
      computing a plurality of scalograms corresponding to the plurality of omnipolar electrograms;
      computing a plurality of peak-frequency functions corresponding to the plurality of scalograms; and
      defining an orientation exhibiting a maximum peak frequency of the plurality of peak-frequency functions as the optimized omnipole orientation for the respective EP data point; and outputting on the display a graphical representation that facilitates visualization of one or more conduction gaps in the lesion using the metrics.

2. The method according to claim 1, wherein receiving the plurality of electrophysiology (EP) data points at an electroanatomical mapping system comprises:
receiving an EP data set at the electroanatomical mapping system, wherein the EP data set corresponds to an anatomical region; and
using the electroanatomical mapping system to bound the EP data set to a region of interest within the anatomical region, wherein the plurality of EP data points fall within the region of interest.

3. The method according to claim 1, wherein the metric comprises a peak-frequency value for the respective EP data point.

4. The method according to claim 1, wherein computing a plurality of scalograms corresponding to the plurality of omnipolar electrograms comprises applying a continuous wavelet transformation to the plurality of omnipolar electrograms to compute the plurality of scalograms.

5. The method according to claim 4, wherein the continuous wavelet transformation utilizes a high time-resolution mother wavelet.

6. The method according to claim 5, wherein the high time-resolution mother wavelet comprises a Paul wavelet.

7. The method according to claim 1, wherein defining the orientation exhibiting the maximum peak frequency of the plurality of peak-frequency functions as the optimized omnipole orientation for the respective EP data point comprises:
generating a curve relating peak frequency to omnipole orientation; and
defining an omnipole orientation at which the curve reaches a maximum as the optimized omnipole orientation for the respective EP data point.

8. The method according to claim 1, wherein the graphical representation comprises at least one of a graphical representation a near-field activity map and a graphical representation of a near-field activation map.

9. The method according to claim 8, wherein the graphical representation of the near-field activity map depicts values of a peak-frequency metric relative to at least one of a near-field frequency threshold and a far-field frequency threshold.

10. The method according to claim 9, wherein the graphical representation of the near-field activity map facilitates visualization of the one or more conduction gaps in the lesion set by highlighting regions where the peak-frequency metric exceeds the near-field frequency threshold.

11. The method according to claim 8, wherein the graphical representation of the near-field activation map depicts a plurality of local activation times (LATs), wherein each LAT of the plurality of LATs is computed for the optimized omnipole orientation for a respective EP data point.

12. A system for mapping conduction activity in a tissue, comprising:
a high-density grid catheter;
a display; and
a mapping and visualization module configured to:
receive a plurality of electrophysiology (EP) data points, wherein each EP data point of the plurality of EP data points includes electrophysiological signals measured by the high-density grid catheter;
compute a peak-frequency metric for each EP data point using the electrophysiological signals for the respective EP data point by executing a process comprising:
computing a plurality of omnipolar electrograms for the respective EP data point using the electrophysiological signals for the respective EP data point;
computing a plurality of scalograms corresponding to the plurality of omnipolar electrograms for the respective EP data point;
computing a plurality of peak-frequency functions corresponding to the plurality of scalograms;
identifying an orientation exhibiting a maximum peak frequency of the plurality of peak-frequency functions as an optimized omnipole orientation for the respective EP data point; and
defining a peak-frequency metric at the optimized omnipole orientation as the peak-frequency metric for the respective EP data point; and
output on the display a graphical representation that facilitates visualization of one or more conduction activities in scar tissue using the metrics.

13. The system according to claim 12, wherein the graphical representation comprises at least one of a graphical representation of a near-field activity map and a graphical representation of a near-field activation map.

14. The system according to claim 12, wherein the mapping and visualization module is further configured to:
receive an EP data set corresponding to an anatomical region; and
bound the EP data set to a region of interest within the anatomical region, wherein the plurality of EP data points fall within the region of interest.

15. A method of mapping local conduction activity in a tissue, comprising:
receiving a plurality of electrophysiology (EP) data points at an electroanatomical mapping system including a high-density grid catheter and a display, wherein each EP data point of the plurality of EP data points includes electrophysiological signals measured by the high-density grid catheter;
computing, with the electroanatomical mapping system, a peak-frequency metric at an optimized omnipole orientation for each EP data point using the electrophysiological signals for the respective EP data point according to a process comprising:
computing a plurality of omnipolar electrograms for a respective EP data point using the electrophysiological signals for the respective EP data point;
computing a plurality of scalograms corresponding to the plurality of omnipolar electrograms for the respective EP data point;
computing a plurality of peak-frequency functions corresponding to the plurality of scalograms; and
identifying an orientation exhibiting a maximum peak frequency of the plurality of peak-frequency functions as an optimized omnipole orientation for the respective EP data point; and
defining a peak-frequency metric at the optimized omnipole orientation as the peak-frequency metric for the respective EP data point; and
outputting on the display a graphical representation of the peak-frequency metric that facilitates visualization of near-field conduction activity in the tissue.

* * * * *